United States Patent
Fröhling

(10) Patent No.: US 6,254,647 B1
(45) Date of Patent: Jul. 3, 2001

(54) PROCESS FOR THE PREPARATION OF A COMPOSITION FOR THE DYEING OF HUMAN HAIR

(75) Inventor: Beate Fröhling, Bensheim (DE)

(73) Assignee: Goldwell GmbH (DE)

( * ) Notice: Subject to any disclaimer, the term of this patent is extended or adjusted under 35 U.S.C. 154(b) by 0 days.

(21) Appl. No.: 09/453,683

(22) Filed: Dec. 3, 1999

(30) Foreign Application Priority Data

Jan. 19, 1999 (DE) ............................................. 199 01 886

(51) Int. Cl.⁷ ...................................................... A61K 7/13
(52) U.S. Cl. ..................................................... 8/406; 8/580
(58) Field of Search ............................... 8/405, 406, 580

(56) References Cited

U.S. PATENT DOCUMENTS

| | | | |
|---|---|---|---|
| 3,811,830 | * 10/1998 | DeMarco | ................... 8/405 |
| 3,898,032 | * 8/1975 | Edman et al. | ........................... 8/408 |
| 4,173,453 | * 11/1979 | Shiah | ....................... 8/405 |
| 4,381,920 | * 5/1983 | Garlen et al. | ........................... 8/406 |
| 5,221,286 | * 6/1993 | Singleton et al. | ....................... 8/406 |
| 5,480,459 | * 1/1996 | Mager et al. | ........................... 8/408 |
| 5,560,859 | * 10/1996 | Hartmann et al. | ........................ 8/405 |
| 5,578,298 | * 11/1996 | Berthiaume et al. | ........... 424/70.122 |
| 5,589,177 | * 12/1996 | Herb et al. | ........................... 424/401 |
| 5,716,418 | * 2/1998 | Matzik et al. | ............................. 8/406 |
| 5,817,155 | * 10/1998 | Yasuda et al. | ............................ 8/406 |
| 5,888,251 | * 3/1999 | Fogg et al. | ................................ 8/405 |

FOREIGN PATENT DOCUMENTS

283027 * 10/1990 (DD) .

* cited by examiner

Primary Examiner—Caroline D. Liott
(74) Attorney, Agent, or Firm—Norris, McLaughlin & Marcus P.A.

(57) ABSTRACT

A time and energy saving process for the preparation of a stable, aqueous emulsion for the dyeing of human hair comprises a) first heating a water phase containing water-soluble surfactants, salts and optionally other water-soluble additives to 50° and 90° C.; subsequently, b) while maintaining this temperature, adding solid fatty components having a melting point between 20° C. and the temperature actually applied according to a) between 50° and 90° C., stirring at this temperature until the solid fatty components are completely melted in the mixture, and, c) adding the remaining liquid fatty components to the composition thus obtained without any further heating.

3 Claims, No Drawings

PROCESS FOR THE PREPARATION OF A COMPOSITION FOR THE DYEING OF HUMAN HAIR

BACKGROUND OF THE INVENTION

The present invention concerns a process for the preparation of a composition for the dyeing of human hair on the basis of a fine, aqueous emulsion, comprising at least one oxidation dyestuff precursor.

Compositions for the permanent dyeing of human hair on the basis of oxidation dyestuff precursors are wide-spread. In general, their application is carried out by a method wherein a composition, usually in form of an aqueous emulsion, comprising at least one oxidation dyestuff precursor, and generally at least one developing and at least one coupling substance, is mixed shortly before application with a composition comprising a peroxide, the mixture then being applied to the hair.

Preparation of this emulsion is carried out by hot emulsification of the components and subsequent cooling, which naturally takes some time, while not always leading to stable emulsions.

SUMMARY OF THE INVENTION

The invention therefore starts from the task of avoiding these problems and providing a process for the preparation of hair dyeing emulsions which saves time and energy, whereby the obtained emulsions also ensure good mixability with the oxidation agent composition, i.e. with aqueous hydrogen peroxide, which, in turn, leads to even distribution of the ready-to-use hair dyeing composition on the hair and thereby to good coloration results.

DETAILED DESCRIPTION OF THE INVENTION

According to the invention, this problem is solved by applying a process for the preparation of a hair dyeing composition in form of a stable, aqueous emulsion wherein a) first the water phase containing the water-soluble surfactants, salts and, optionally other water-soluble additives, in particular oxidation dyestuff precursors, is heated to between 50° and 90° C., in particular to about 60° to 80° C.; then, b) while maintaining this temperature, fatty components having a melting point between 20° C. and the applied temperature in step a) ranging between 50° and 90° C. are stirred into the water phase; stirring and temperature being upheld until these fatty-phase components are completely melted, and c) the remaining liquid fatty-phase components are added to the composition thus obtained while the temperature slowly decreases.

Compared to the customarily used hot emulsion technology, this process allows essential savings of time and energy, and thereby also cost savings, as it only requires initial heating with subsequent cooling of approximately 30% of the fatty phase and app. 80% of the total emulsion, whereby cooling also ensues faster due to the separate addition of the liquid fatty-phase components.

The preferred weight proportion of the fatty phase to the water phase in the ready-to-use dyeing emulsion ranges from about 20 to 80 and 50 to 50, in particular from about 25 to 75 and 40 to 60; the preferred weight proportion of solid to liquid fatty-phase components ranging from about 3 to 1 and 1 to 3, preferably from about 2 to 1 and 1 to 2.

The preferred liquid substances in the fatty phase are those fatty acids being liquid, for example, at room temperature, i.e., about 20% to 25° C., in particular oleic acid. The preferred amount of these fatty acids is about 5% to 15%, in particular about 6% to 12% by weight, calculated to the total composition.

Further preferred liquid components of the fatty phase are $C_{10}$–$C_{22}$-fatty alcohol ethoxylates, preferably lauryl, coco and oleyl alcohol ethyleneoxide condensates in an amount from about 5% to 25%, in particular about 10% to 20%, for example about 15% by weight, calculated to the total composition.

Also useful are liquid sugar fatty acid esters, such as saccharose and glucose diesters, in particular dioleates, for example glucose and methyl glucose dioleate in an amount from about 5% to 25%, for example about 10% to 15% by weight, calculated to the total composition.

Further useful components are liquid fatty alcohols, such as oleyl alcohol and polyols, for example, glycerol and propylene glycol.

Suitable solid fatty phase components having a melting point between 20° C., preferably 25° to 30° C., and the temperature from 50° to 90° C. to which the water phase is adjusted at the time of their incorporation in finely-distributed form, are in particular emulsifiers and fatty substances, for example, higher fatty alcohols, such as myristyl alcohol, cetyl alcohol, stearyl alcohol and fatty alcohol mixtures, higher fatty acid esters, such as glycerol, ethanediol and propanediol fatty acid esters, for example, ethanediol mono- and distearate, 1.2-propyleneglycol mono- and distearate as well as glyceryl stearate.

Further suitable solid fatty phase components are higher fatty acid mono- and dialkanolamides, such as coco fatty acid and stearic acid monoethanolamide. Preferably used are mixtures of these substances with surface-active properties.

The viscosity of the hair dyeing emulsions prepared according to the invention preferably ranges from about 5,000 to 30,000, in particular from about 10,000 to 25,000, for example, from about 15,000 to 20,000mPa•s, measured at 20° C. in a Brookfield Viscosimeter RVT.

The water phase can comprise water-soluble emulsifiers. Useful as such are in particular anionic surfactants.

Anionic surfactants suitable within the scope of the invention are present in particular in an amount from about 0.25% to 5% by weight, preferably about 0.4% to 2.5% by weight, calculated to the total composition (of the ready-to-use emulsion).

These are anionic surfactants of the sulfate, sulfonate, carboxylate and alkyl phosphate type, especially, of course, those customarily used in hair treatment compositions, in particular, the known $C_{10}$–$C_{18}$-alkyl sulfates, and the respective ether sulfates, for example, $C_{12}$–$C_{14}$-alkyl ether sulfate, lauryl ether sulfate, especially with 1 to 4 ethylene oxide groups in the molecule, acyl aminocarboxylic acids, such as lauroyl sarcosinate and glutamate, furthermore monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

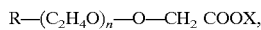

wherein R is a $C_8$–$C_{20}$-alkyl group, preferably a $C_{12-C14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

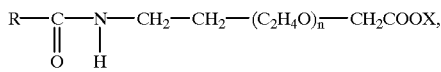

wherein R and X have the above meanings, and n stands in particular for a number from 1 to 10, preferably 2.5 to 5.

Such products have been known for some time and are on the market, for example, under the trade name "AKYPO®" and "AKYPO-SOFTQ®".

Also useful are $C_{8-C20}$-acyl isethionates, alone or in admixture with other surfactants, and sulfofatty acids and the esters thereof.

It is also possible to use amphoteric or zwitterionic surfactants as water-soluble emulsifiers, in particular also in admixture with anionic surfactants, whereby the total amount should preferably range from about 0.25% to 5%, in particular about 0.5% to 2.5% by weight, calculated to the total hair dyeing emulsion.

Useful as such are in particular the various known betaines such as fatty acid amido alkyl betaines and sulfobetaines, for example, lauryl hydroxy sulfobetaine; long-chain alkyl amino acids, such as cocoaminoacetate, cocoaminopropionate and sodium cocoamphopropionate and -acetate have also proven suitable. In detail it is possible to use betaines of the structure

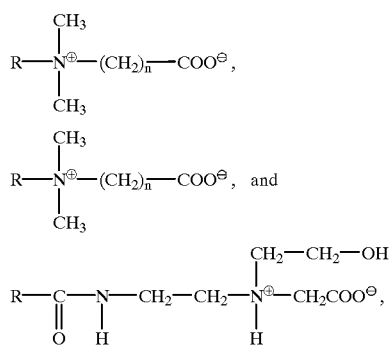

wherein R is a $C_{8-C18}$-alkyl group and n is 1 to 3; sulfobetaines of the structure

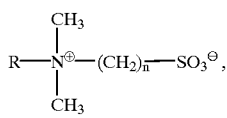

wherein R is a $C_8$–$C_{18}$-alkyl group and n is 1 to 3; and amidoalkyl betaines of the structure

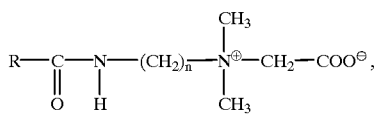

wherein R is a $C_8$–$C_{18}$-alkyl group and n is 1 to 3.

Also useful are nonionic, water-soluble surfactants, for example, from $C_{8-C18}$-alkyl polyglucosides with a polymerization degree of 1 to 5, in the named amounts alone or in admixture with anionic and/or amphoteric or zwitterionic surface-active substances.

Aminoxides are also useful.

Further useful surfactants are also cationic surfactants, such as the known quaternary ammonium compounds with one or two alkyl or alkenyl groups with 10 to 22 carbon atoms in the molecule, in particular in an amount from 0.1% to 7.5%, preferably 0.25% to 5%, especially preferred 0.5% to 2.5% by weight, calculated to the total composition.

Suitable long-chain quaternary ammonium compounds which can be used alone or in admixture are in particular cetyl trimethyl ammonium chloride, dimethyl dicetyl ammonium chloride, trimethyl cetyl ammonium bromide, behenyl trimonium chloride, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, cetyl pyridinium chloride, etc.

Basically suitable are all quaternary ammonium compounds listed under the generic name "Quaternium" in the CTFA International Cosmetic Ingredient Dictionary.

The hair dyeing emulsion according to the invention comprises at least one oxidation dyestuff precursor; useful is a mixture of at least one developing and at least one coupling substance.

These are known per se and described, for example, in the monography of K. Schrader, "Grundlagen und Rezepturen der Kosmetika", 2nd Ed. (1989), pp. 784–799.

Examples of developing substances are in particular 1.4-diaminobenzene, 2.5-diaminotoluene, tetraaminopyrimidines, triaminohydroxypyrimidines, 1.2.4-triaminobenzene, 2-(2.5-diamino-phenyl)ethanol, 2-(2'-hydroxyethyl amino)-5-aminotoluene and 1amino-4-bis-(2'-hydroxyethyl)-aminobenzene, or the water-soluble salts thereof; examples for coupling substances are resorcinol, 2-methyl resorcinol, 4-chlororesorcinol, 2-amino-4-chlorophenol, 4-(N-methyl) aminophenol, 2-aminophenol, 3-aminophenol, 1-methyl-2-hydroxy-4-aminobenzene, 3-N,N-dimethyl aminophenol, 4-amino-3-methyl phenol, 5-amino-2-methyl phenol, 6-amino-3-methyl phenol, 3-amino-2-methyl amino-6-methoxypyridine, 2-amino-3-hydroxypyridine, 4-aminodiphenylamine, 4.4'-diaminodiphenylamine, 2-dimethyl amino-5-aminopyridine, 2.6-diaminopyridine, 1.3-diaminobenzene, 1-amino-3-(2'-hydroxyethyl amino)benzene, 1-amino-3-[bis (2'-hydroxyethyl) amino]benzene, 1.3-diaminotoluene, α-naphthol, 1.4-diamino-2-chlorobenzene, 4.6-dichlororesorcinol, 4-hydroxy-1.2-methylene dioxybenzene, 1.5-dihydroxynaphthaline, 1.7-dihydroxynaphthaline, 2.7-dihydroxynaphthaline, 1-hydroxynaphthaline, 4-hydroxy-1.2-methylene dioxybenzene, 2.4-diamino-3-chlorophenol, and/or 1-methoxy-2-amino-4-(2'-hydroxyethyl amino) benzene, whereby this list is just exemplary.

Developing and coupling substances are preferably contained in a molar proportion of 1:3 to 5:1. in particular about 1:1 and about 3:1; their proportion in the hair dyeing emulsions according to the invention may range from about 0.1% to about 5% by weight, depending on the desired coloration.

It is useful to incorporate these oxidation dyestuff precursors already into the aqueous phase, however, if desired, they can also be added to the finished product.

Optionally, the compositions prepared according to the invention can also comprise so-called shading agents for the fine-tuning of the desired shade, in particular also direct-acting dyestuffs.

Such shading agents are, for example, nitro dyestuffs, such as 2-amino-4.6-dinitrophenol, 2-amino-4-nitrophenol, 2-amino-6-chloro-4-nitrophenol, etc., preferably in amounts ranging from about 0.05% to 2.5%, in particular 0.1% to 1% by weight, calculated to the dyeing composition (excluding the oxidation composition).

The hair dyeing composition emulsions prepared according to the invention can comprise basic substances and additives customarily found in such compositions, conditioning agents, stabilizers, fats and oils, thickening agents, complexing agents, etc., known as state of the art and described, for example, in the monography of K. Schrader, "Grundlacen und Rezepturen der Kosmetika", 2nd Ed. (Htithig Buch Verlag, Heidelberg, 1989), pp. 782 to 815.

The hair dyeing emulsions prepared according to the invention preferably have a pH-value in the alkaline range, in particular between about 8 and about 12.5, preferably between 8.5 and 11.

For application, the oxidation dyestuff precursor emulsion prepared according to the invention is mixed with an oxidation agent composition. The preferred oxidation agent is hydrogen peroxide, for example, in concentrations between 2% to 6%.

However, it is also possible to use other peroxides, such as urea peroxide and melamine peroxide.

The pH-value of the ready-to-use hair dyeing composition, i.e. after admixture with peroxide, may be in the slightly acidic range, i.e. between 5.5 to 6.9, as well as in the neutral range and in the alkaline range, i.e. between pH 7.1 and 10.

Following are Examples which illustrate the invention.

EXAMPLE 1

An aqueous phase, consisting of:

| | |
|---|---|
| Ammonia, 25% | 92.00(partsbyweight) |
| Pyrogenic silica | 1.00 |
| Sodium lauryl sulfate | 5.00 |
| EDTA (Trisodium salt) | 2.00 |
| Ammonium chloride | 5.00 |
| Sodium sulfite | 10.00 |
| Ascorbic acid | 5.00 |
| Cationic plant protein hydrolyzate | 4.50 |
| Panthenol | 6.00 |
| Hop extract | 5.00 |
| Perfume | 3.60 |
| and the oxidation dyestuff precursors | |
| p-Toluylenediamine sulfate | 5.40 |
| Resorcinol | 0.59 |
| 4-Chlororesorcinol | 1.65 |
| 3-Aminophenol | 0.25 |
| 3-Hydroxy-4-methyl aniline | 0.05 |

-continued

| | |
|---|---|
| and 6-hydroxy-2.4.5-triaminopyrimidine sulfate | 0.10 |
| as well as | |
| Water | 595.95 | was heated to about 65° C., and into this hot solution was stirred the following mixture of solid fatty components, which disperse into this hot water phase by melting:

| | |
|---|---|
| Cetyl stearyl alcohol/Sodium cetyl stearyl sulfate (9:1) | 120.00(partsbyweight) |
| Stearic acid monoethanolamide | 23.00 |
| Coco fatty acid monoethanolamide | 23.00 |

Subsequently the following liquid fatty-phase components were stirred into the above composition without further heating:

| | |
|---|---|
| Oleth-5 | 50.00(partsbyweight) |
| Oleic acid | 25.00 |
| 1.2-Propanediol | 10.00 |

A fine-component, stable emulsion was obtained, which resulted in a permanent medium-blond coloration upon application with a diluted hydrogen peroxide solution or emulsion.

EXAMPLE 2

Into 680 parts by weight of the water phase as described in Example 1 100 parts by weight of a pulverulent mixture of 70 parts by weight glycol distearate and 30 parts by weight glyceryl stearate were added under stirring at 60° C., with following addition, without any more heating, of 220 weight parts of a liquid mixture of 120 parts by weight Laureth-2 and 100 parts by weight oleic acid.

A fine, stable, dye emulsion was again obtained, showing good mixing capability with liquid hydrogen peroxide compositions, thus forming a hair dyeing composition which resulted in a long-lasting medium-blond coloration on the hair.

What is claimed is:

1. Process for the preparation of a stable, aqueous emulsion for the dyeing of human hair, comprising the steps of, in order;

(a) heating a water phase comprising water-soluble additives to a chosen temperature between 50° and 90° C., the water phase comprising at least one oxidation dyestuff precursor, (b) adding solid fatty components having a melting point between 20° C. and the chosen temperature of step (a)

(c) stirring and maintaining the chosen temperature until the fatty components of step (b) are completely melted and (d) adding liquid fatty-phase components to the composition of step (c), without any further heating, to thereby form the emulsion.

2. Process according to claim 1, wherein the chosen temperature is between about 60° and 80° C.

3. Process according to claim 1, wherein the water-soluble additives are water-soluble surfactants and/or salts.

* * * * *